United States Patent
Kim (10) Patent No.: US 7,326,474 B2
(45) Date of Patent: Feb. 5, 2008

(54) LUMINESCENT SPIRO-DIMER AND ORGANIC LIGHT-EMITTING DEVICE COMPRISING THE SAME

(75) Inventor: Jung-Soo Kim, Yongin-si (KR)

(73) Assignee: Neoviewkolon Co., Ltd., Hongseong-Gun (KR)

( * ) Notice: Subject to any disclaimer, the term of this patent is extended or adjusted under 35 U.S.C. 154(b) by 200 days.

(21) Appl. No.: 10/524,410

(22) PCT Filed: Aug. 14, 2003

(86) PCT No.: PCT/KR03/01640

§ 371 (c)(1),
(2), (4) Date: Feb. 14, 2005

(87) PCT Pub. No.: WO2004/016709

PCT Pub. Date: Feb. 26, 2004

(65) Prior Publication Data

US 2005/0238909 A1   Oct. 27, 2005

(30) Foreign Application Priority Data

Aug. 16, 2002  (KR) .............. 10-2002-0048545

(51) Int. Cl.
  *H01J 1/62*   (2006.01)
  *C09K 11/06*  (2006.01)

(52) U.S. Cl. ............... 428/690; 428/917; 313/504; 313/506; 252/301.16

(58) Field of Classification Search ............... 428/690, 428/917; 313/504, 506; 257/40, E51.049, 257/E51.051; 564/426; 585/26, 27
See application file for complete search history.

(56) References Cited

U.S. PATENT DOCUMENTS

| 5,763,636 | A  | 6/1998  | Kreuder et al. |
| 6,132,641 | A  | 10/2000 | Rietz et al. |
| 6,329,082 | B1* | 12/2001 | Kreuder et al. ............. 428/690 |
| 6,361,884 | B1 | 3/2002  | Kreuder et al. |
| 6,808,826 | B2 | 10/2004 | Kim et al. |
| 6,984,462 | B2* | 1/2006  | Kim et al. .................. 428/690 |

FOREIGN PATENT DOCUMENTS

| KR | 2002-0030371 A | 4/2002 |
| WO | WO-97/31048 A1 | 8/1997 |
| WO | WO-99/40655 A1 | 8/1999 |

* cited by examiner

Primary Examiner—Milton I. Cano
Assistant Examiner—Camie S. Thompson
(74) Attorney, Agent, or Firm—Birch, Stewart, Kolasch & Birch, LLP (57) ABSTRACT

A luminescent spiro-dimer which has a superior heat-resistance and is capable of emitting high quality blue light, and an organic light-emitting device including the same are disclosed. The luminescent spiro-dimer has the structure of the following chemical formula, and the organic light-emitting device includes the first electrode having a high work function; the second electrode having a low work function; and at least one organic layer formed between the first electrode and the second electrode, which includes the spiro-dimer, wherein, K is a linking group, and R is H, halogen, CN, $CO_2R^*$, $OR^*$, $NR^*_2$, $SR^*$, alkyl, aryl, heteroaryl, heterocyclic or fused ring group, and $R^*$ is H, halogen, alkyl, alkenyl, aryl, heteroaryl, or heterocyclic group.

16 Claims, 1 Drawing Sheet

LUMINESCENT SPIRO-DIMER AND ORGANIC LIGHT-EMITTING DEVICE COMPRISING THE SAME

FIELD OF THE INVENTION

The present invention relates to a luminescent spiro-dimer, and more particularly, to a luminescent spiro-dimer which has a superior heat-resistance and is capable of emitting high quality blue light, and an organic light-emitting device (OLED) including the same.

BACKGROUNDS OF THE INVENTION

An organic light-emitting device, which is generally called as EL (Electroluminescence device), is one of the representative flat-panel display devices along with Liquid Crystal Display(LCD), Plasma Display Panel(PDP), and Field Emission Display(FED). The organic light-emitting device does not require a back-light for light-emitting, and can be manufactured into a thin film and flexible device, and mass-produced by the well-known film fabrication techniques. In addition, the EL is a self-light emitting device. Therefore, the EL has not only a fast response speed but also an excellent brightness and wide viewing angle. Also, the EL can be operated with a low driving voltage, and display full colors in a visible region. In the organic light-emitting device, an organic light-emitting layer having a light-emitting property is interposed between a transparent electrode made of ITO et al. having a high work function and a metal electrode made of Mg et al. having a low work function. When a voltage is applied to the electrodes, holes and electrons are generated at the electrodes, and recombined at the organic light-emitting layer to induce a light-emission. To produce a full-color organic light-emitting device, it is necessary to prepare organic light-emitting compounds for emitting red(R), green(G) or blue(B) light.

A Spiro compound is one of the well-known organic light-emitting compounds. For example, U.S. Pat. No. 5,840,217 discloses spiro-single compounds such as spiro-triphenylamine, spiro-N,N'-diphenyl-N,N'-bis(3-methylphenyl)-1,1'-biphenyl-4,4'-diamine (spiro-TPD), spiro-benzoxazole, spiro-sexiphenyl, and so on. U.S. Pat. No. 5,741,921 discloses spiro-compounds in which the spiro atom of the spiro-compound is Sn, Si, or so on instead of carbon. U.S. Pat. No. 6,211,369 discloses spiro-compounds in which at least one aromatic groups of the spiro-compound is a heteroaryl group. U.S. Pat. Nos. 5,621,131 and 5,763,636 disclose spiro-polymers in which the repeating unit of the polymer is a spiro-compound. Also, Japanese Laid-open patent No. 2001-131434 discloses organic light-emitting compounds in which two aromatic groups are linked with an anthracene group. These conventional spiro-compounds have a good heat-resistance, but the blue light emitting efficiency thereof is not satisfactory. Furthermore, it is not easy to form a layer with the spiro-compounds by a conventional vacuum deposition process. Thus, the organic light-emitting layer made of the spiro-compounds is conventionally manufactured by a spin-coating process, which decreases the productivity of the organic light-emitting device.

SUMMARY OF THE INVENTION

Therefore, it is an object of the present invention to provide a luminescent spiro-dimer which is capable of emitting high quality blue light, and has a superior heat-resistance and light emitting efficiency, and an organic light-emitting device comprising the same.

It is other object of the present invention to provide a luminescent spiro-dimer which is capable of forming a layer by various conventional film fabrication techniques, and obviates the disadvantages of the conventional spiro-single compounds and spiro-polymers, and an organic light-emitting device comprising the same.

It is another object of the present invention to provide a luminescent spiro-dimer which can be used to form a blue light-emitting layer and/or a hole-injecting/transporting layer, and an organic light-emitting device comprising the same.

In order to achieve these objects, the present invention provides a novel luminescent spiro-dimer of the following chemical formula. The present invention also provides an organic light-emitting device comprising: the first electrode having a high work function; the second electrode having a low work function; and at least one organic layer formed between the first electrode and the second electrode, which includes the luminescent spiro-dimer of the following chemical formula, wherein, the linking group K is in which n can be the same or different, and is an integer of 0 to 6, or in which n can be the same or different, and is an integer of 0 to 4; R can be the same or different, and is H, halogen, CN, $CO_2R^*$, $OR^*$, $NR^*_2$, $SR^*$, substituted or non-substituted alkyl group containing from 1 to 4 carbon atoms, substituted or non-substituted aryl or heteroaryl group containing from 4 to 24 carbon atoms, substituted or non-substituted heterocyclic group containing from 4 to 24 carbon atoms, or substituted or non-substituted fused ring group containing from 4 to 24 carbon atoms; and R* can be the same or different, and is H, halogen, substituted or non-substituted alkyl or alkenyl containing from 1 to 6 carbon atoms, substituted or non-substituted aryl or heteroaryl group containing from 4 to 24 carbon atoms, or substituted or non-substituted heterocyclic group containing from 4 to 24 carbon atoms.

Preferably, the linking group K is a chemical bond, and $R_1$ and $R_2$ can be the same or different, and are H, halogen, CN, or alkyl, aryl, alkoxy or heteroaryl group containing from 1 to 10 carbon atoms.

DETAILED DESCRIPTION OF THE INVENTION

A more complete appreciation of the invention, and many of the attendant advantages thereof, can be better appreciated by reference to the following detailed description and the accompanying drawings.

The luminescent spiro-dimer of the present invention absorbs the energy generated by the recombination of electrons and holes, and emits light using the absorbed energy. The spiro-dimer of the present invention can be represented by the following chemical formula 1.

[Chemical Formula 1]

In Chemical formula 1, the linking group K is in which n can be the same or different, and is an integer of 0 to 6, or in which n can be the same or different, and is an integer of 0 to 4. Preferably, the linking group K is a chemical bond, and $R_1$ and $R_2$ can be the same or different, and are H, halogen, CN, or alkyl, aryl, alkoxy or heteroaryl group containing from 1 to 10 carbon atoms.

R can be the same or different, and is H, halogen, CN, $CO_2R^*$, $OR^*$, $NR^*_2$, $SR^*$, substituted or non-substituted alkyl group containing from 1 to 4 carbon atoms, substituted or non-substituted aryl or heteroaryl group containing from 4 to 24 carbon atoms, substituted or non-substituted heterocyclic group containing from 4 to 24 carbon atoms, or substituted or non-substituted fused ring group containing from 4 to 24 carbon atoms, and R* can be the same or different, and is H, halogen, substituted or non-substituted alkyl or alkenyl containing from 1 to 6 carbon atoms, substituted or non-substituted aryl or heteroaryl group containing from 4 to 24 carbon atoms, or substituted or non-substituted heterocyclic group containing from 4 to 24 carbon atoms.

An example of the luminescent spiro-dimer of the present invention is the compound represented by the following chemical formula 2.

[Chemical formula 2]

In chemical formula 2, L can be the same or different, and is H, in which n can be the same or different, and is an integer of 0 to 6, in which n can be the same or different, and is an integer of 0 to 6, or and $R_1$ can be the same or different, and is H, or alkyl, aryl, alkoxy or heteroaryl group containing from 1 to 10 carbon atoms. More preferably, L is In the present invention, the spiro-compound means a compound in which two rings are bonded to a tetravalent atom, and the tetravalent atom is called as a spiro-atom. The wavelength of the light emitted from the spiro-dimer, and the charge transporting/injecting properties of the spiro-dimer are changed according to the substituent and the linking group of the spiro-dimer. Therefore, the physical properties of an organic layer, such as the wavelength of the emitted light, charge transporting property, and so on, can be controlled by changing the substituent and the linking group of the spiro-dimer. Particularly, the spiro-dimer of the present invention obviates the disadvantages of the conventional spiro-single compounds and spiro-polymers, and has a superior heat-resistance and is capable of forming an organic layer by various conventional film fabrication techniques. Therefore, the spiro-dimer of the present invention increases the productivity and life span of the organic light-emitting device, and emits high quality blue light, and useful for forming various organic layers of an organic light-emitting device.

The luminescent spiro-dimer of the present invention can be prepared by various conventional methods. The method for producing a spiro-compound is well-known in the art (For example, see JSDS July, 1978, 307 and U.S. Pat. No. 5,840,217). The direct linking of spiro-compounds, introduction of aryl substituent, or linking of a spiro-compound with the linking group K can be carried out by Suzuki-coupling reaction (For example, see JOC, 1996, 61, 3127). The vinyl group can be introduced to the spiro-compound by the well-known Wittig reaction (For example, see "Vogel's Textbook of Practical Organic Chemistry", 4th Ed., Longman (1978) p338).

Figure 1:
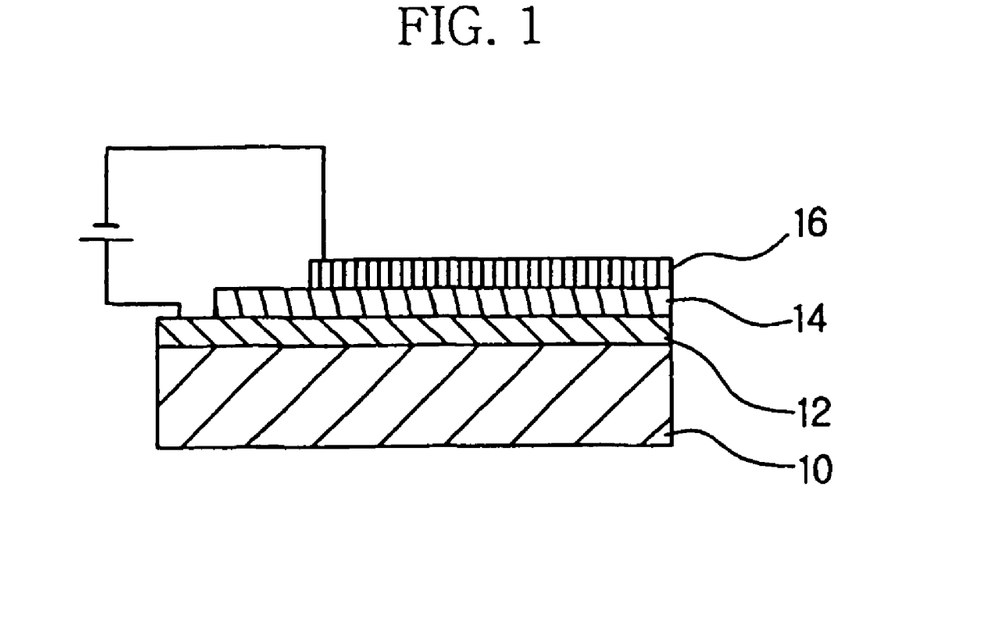
FIG. 1 is a cross sectional view of the organic light-emitting device according to an embodiment of the present invention.

FIG. 1 is a cross sectional view of the organic light-emitting device including the luminescent spiro-dimer according to an embodiment of the present invention. As shown in FIG. 1, the first electrode 12 (anode) having a high work function is formed on a substrate 10, and at least one light-emitting layer 14 including the luminescent spiro-dimer of the present invention is formed on the first electrode 12. The luminescent spiro-dimer of the present invention can be used as a host material or a dopant of the organic light-emitting layer 14. Furthermore, the light-emitting layer 14 can include a conventional organic light-emitting compound, a fluorescent dye, a host and/or dopant material in addition to the luminescent spiro-dimer of the present invention. When the compound of the present invention is used as a dopant with the conventional host material, such as $Alq_3$, the preferable amount of the dopant is 2 to 50% by weight. On the light-emitting layer 14, the second electrode 16 (cathode) having a low work function is formed so that the second electrode 16 faces toward the first electrode 12. When a voltage is applied between the first electrode 12 and the second electrode 16 of the organic light-emitting device, the holes and the electrons produced in the first and the second electrodes 12, 16 are injected into the light-emitting layer 14. The injected holes and the electrons are recombined in the layer 14 to induce the light emission. If the organic light-emitting device is designed to emit light at the side of the first electrode 12, the substrate 10 should be made of a transparent material, preferably a glass or a transparent plastic film. In this case, the emitted light produces a display image by passing through the transparent first electrode 12 and the transparent substrate 10. The substrate 10 of the organic light-emitting device is made of an electrically insulating material. The first electrode 12 can be made of the material having a high work function, for example, Indium Tin Oxide (ITO), polyaniline or Ag. The second electrode 16 can be made of the material having a low work function, for example, a metal such as Al, Mg or Ca, or a metal alloy such as Li—Al or Mg—Ag.

Figure 2:
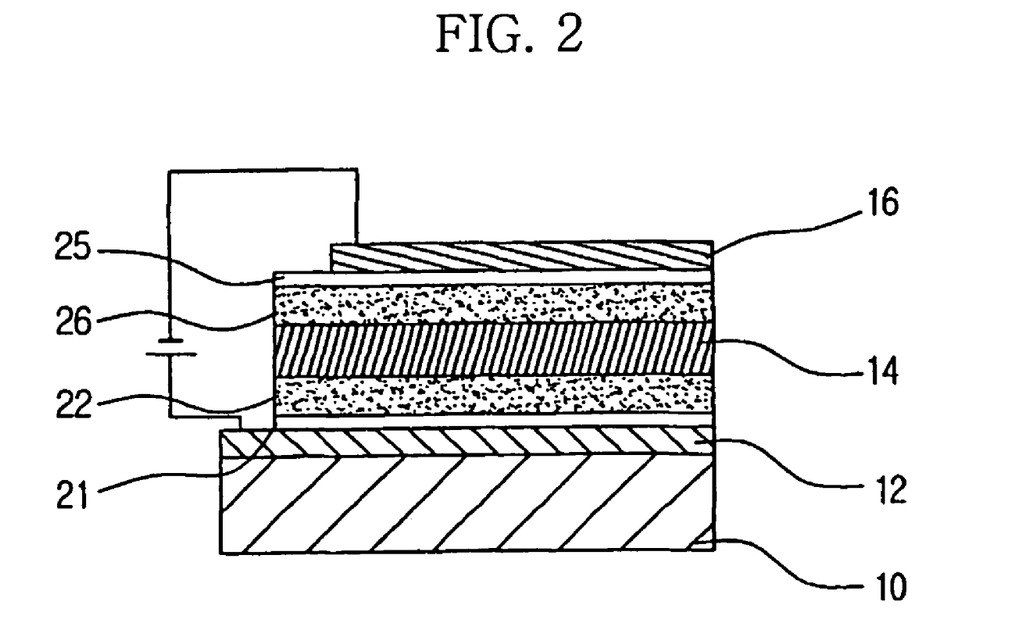
FIG. 2 is a cross sectional view of the organic light-emitting device according to other embodiment of the present invention.

FIG. 2 is a cross sectional view of the organic light-emitting device according to other embodiment of the present invention. In contrast to the organic light-emitting device shown in FIG. 1, the organic light-emitting device shown in FIG. 2 further includes a hole injecting layer 21 and a hole transporting layer 22 formed between the first electrode 12 and the light-emitting layer 14 to facilitate the injection and transportation of holes from the first electrode 12 into the light-emitting layer 14, and an electron injecting layer 25 and an electron transporting layer 26 formed between the second electrode 16 and the light-emitting layer 14 to facilitate the injection and transportation of electrons from the second electrode 16 into the light-emitting layer 14. The hole injecting layer 21 and the hole transporting layer 22 are provided to facilitate the stable hole injection and transportation, and to prevent the electron flow therethrough. Exemplary material for forming the hole injecting and the hole transporting layers 21, 22 includes porphyrinic compound, such as copper phthalocyanine(CuPc), disclosed in U.S. Pat. No. 4,356,429; tri(phenyldiamine) derivatives such as N,N'-diphenyl-N,N'-bis(3-methylphenyl)-[1,1'-biphenyl]-4,4'-diamine (TPD); amine derivatives having aromatic condensed ring such as 4,4',4''-tris[3-methylphenyl(phenyl)amino]triphenylamine (m-MTDATA), and N,N'-diphenyl-N,N'-bis(1-naphthylphenyl)-1,1'-biphenyl-4,4'-diamine (α-NPD); N,N,N'N'-tetrakis(m-methylphenyl)-1,3-diaminobenzene (PDA), 1,1-bis[N,N-di(p-tolyl)aminophenyl]cyclohexane (TPAC), styrylamine derivatives, N,N'-bis-(1-naphthyl)-N,N'-diphenylbenzidine, and so on with or without the above-mentioned conventional compounds. The electron injecting layer 25 and the electron transporting layer 26 are provided to facilitate the stable electron injection and transportation, and to prevent the hole flow therethrough. Exemplary material for forming the electron injecting and the electron transporting layers 25, 26 includes LiF, 1,2,4-triazole (TAZ), quinolin derivatives, tris(8-quinolinolate)aluminum (Alq3), and so on. In addition, the luminescent spiro-dimer of the present invention can be used to form the hole injecting layer 21, the hole transporting layers 22, the electron injecting layer 25 or the electron transporting layers 26 with or without the above-mentioned conventional compounds. The function of the luminescent spiro-dimer in an organic light-emitting device is determined according to its relative potential with respect to the neighboring layer(s).

These layers improve the light-emitting efficiency by increasing the amounts of the holes and the electrons injected into the organic light-emitting layer 14, by constraining the holes and the electrons in the light-emitting layer 14, and by accelerating the hole-electron recombination. The thickness of the light-emitting layer 14, the hole injecting layer 21, the hole transporting layer 22, the electron injecting layer 25 or the electron transporting layer 26 can be varied, for example, according to the method for forming the layers or the structure of the produced organic light-emitting device, but the thickness is generally 5-1000 nm, preferably 10-500 nm. The organic layers can be formed by conventional film fabrication processes such as spin coating, vacuum deposition, thermal evaporation, spin casting, sputtering, e-beam evaporation, chemical vapor deposition (CVD) and so on, and preferably by vacuum deposition. The organic layers can be formed with the mixture of at least two compounds by the above-mentioned methods, or by co-depositing two or more compounds. The anode can also be formed by conventional processes, such as sputtering, ion plating, thermal depositing by using e-gun and so on. The metal layer for forming the cathode can be produced by thermal evaporation, sputtering, chemical vapor deposition, ion plating, and so on. The luminescent spiro-dimer of the present invention can be used not only for the organic light-emitting devices shown in FIG. 1 or FIG. 2 but also for the various organic light-emitting devices utilizing the electron-hole recombination for light emission. The various organic light-emitting devices are conventionally known in the art, and for example, disclosed in U.S. Pat. Nos. 4,539,507 and 5,151,629.

Hereinafter, the preferable examples of the present invention are provided for better understanding of the present invention. However, the following examples are to illustrate the present invention, and the present invention cannot be limited by the following examples.

MANUFACTURING EXAMPLE

Synthesis of 9.9'-Spirobifluorene

As shown in the following reaction 1, 6.1 g of 2-bromo-biphenyl and 0.585 g of dried Mg were dissolved with ether, and 4.2 g of fluorenone dissolved in ether was added thereto, and refluxed while stirring overnight. The produced yellow precipitate was filtered, and stirred in cold ammonium chloride, and then the obtained crystal was filtered again and dried. Thereafter, acetic acid was added to the solid product, and the solution was refluxed while stirring. A small amount of hydrochloric acid was added thereto to obtain the solid target compound. The solid target compound was filtered and washed to obtain pure target compound with the yield of 80%.

[Reaction 1]

EXAMPLE 2

Synthesis of Spiro-dimer

As shown in the following reaction 2, 0.5 g(1.3 mmol) of bromo-spiro compound and 0.68 g(1.9 mmol) of spiro boric acid, 0.05 g of Pd(TPP)$_4$ catalyst (wherein, TPP is triphenylphosphine), and 1.3 ml of 2M Na$_2$CO$_3$ were refluxed in 1,2-dimethoxyethane solvent while stirring for 24 hours (Suzuki coupling reaction) to obtain the target compound.

EXAMPLE 3

Synthesis Spiro-dimer Linked with Phenyl Linking Group (1)

0.14 g(0.46 mmol) of 4,4'-dibromobiphenyl, 0.5 g(1.39 mmol) of spiro boric acid, 0.04 g of Pd(TPP)$_4$ catalyst, and 0.92 ml of 2M Na$_2$CO$_3$ were refluxed in 1,2-dimethoxyethane solvent while stirring for 24 hours (Suzuki coupling reaction) to obtain the target compound of the following chemical formula 3.

[Reaction 2]

[Chemical formula 3]

EXAMPLE 4

Synthesis of Spiro-dimer Linked with Phenyl Linking Group (2)

0.15 g(0.32 mmol) of 4,4'-dibromotetraphenyl, 0.34 g(0.96 mmol) of spiro boric acid, 0.03 g of Pd(TPP)$_4$ catalyst, and 0.32 ml of 2M Na$_2$CO$_3$ were refluxed in 1,2-dimethoxyethane solvent while stirring for 24 hours (Suzuki coupling reaction) to obtain the target compound of the following chemical formula 4.

[Chemical formula 4]

EXAMPLE 4

Synthesis of Spiro-DPVBi

As the first step, 10 g of 4-bromobenzylbromide and 13.11 g of triphenylphosphine were refluxed in benzene solvent while stirring overnight to obtain a phosphonium salt. 0.40 g of NaH(60%) was stirred in 10 ml of dimethylsulfoxide (DMSO) at 65° C. for 1 hour to obtain Dymsyl ion, and the reaction solution was cooled to room temperature.

As shown in the following reaction 3, 5.21 g of the obtained phosphonium salt was added to the reaction solution, and the reaction solution was stirred at room temperature for 45 minutes (Reaction i). Then, 2.14 g of acetylspiro compound was added thereto, and stirred overnight at 50° C. to carry out Wittig reaction (Reaction ii). Finally, the obtained product was refluxed while stirring overnight in the presence of 0.36 g of NiCl$_2$(TPP)$_2$, 2.68 g of triphenylphosphine, 0.16 g of bipyridyl, 1.33 g of Zn dust, and DMSO solvent (Reaction iii).

EXAMPLE 5

Synthesis of Spiro-dimer Derivative (1)

5 g of bromobiphenyl was dissolved in 100 mL of tetrahydrofuran(THF), and the solution was cooled to −95° C. Then, 20.2 mL of 1.6M butyllithium was added thereto and stirred for 5 minutes. 24.31 mL of trimethylborate was added thereto at −95° C., and the solution was stirred for 2 hours at −78° C., and for 12 hours at room temperature. Then, 10% HCl solution was added thereto at 0° C. to adjust the pH of the solution to be less than 6, and the solvent was distilled. The reaction product was extracted with ether to obtain biphenylboronic acid. Thereafter, as shown in the following reaction 4, 0.08 g of bromospiro-dimer, 0.034 g of biphenyl boric acid, 0.003 g of Pd(TPP)$_4$ catalyst, 0.11 ml of 2M Na$_2$CO$_3$ were refluxed in 1,2-dimethoxyethane solvent while stirring for 24 hours (Suzuki coupling reaction) to obtain the target compound.

[Reaction 4]

EXAMPLE 6

Synthesis of Spiro-dimer Derivative (2)

0.24 g of spiro acetophenone and 0.074 g of benzaldehyde were stirred in 10 ml of ethanol, and 0.05 g of potassium hydroxide was added thereto, and stirred at room temperature for 24 hours. 0.095 g of phenylhydrazine was added to the solution, and refluxed while stirring for 6 hours. After cooling the reaction solution, the solid product was filtered, and washed with ethanol to obtain the target compound of the following chemical formula 5.

[Chemical formula 5]

EXAMPLE 7

Synthesis Spiro-dimer Linked with Ethenyl Linking Group 180 mL of THF was added to a flask, and cooled to 0° C. 11.1 g(58.5 mmole) of TiCl$_4$ and 7.2 g(110.25 mmole) of Zn powder were added thereto, and stirred at 0° C. for 30 minutes, and refluxed for 30 minutes. Then, 17 g(49 mmol) of spiroaldehyde dissolved in 100 mL of THF was added thereto, and refluxed for 24 hours. After completion of the reaction, 1N—HCl was added, and the reaction solution was filtered to obtain the target compound of the following chemical formula 6. The melting temperature of the obtained compound was 415° C.

[Chemical formula 6]

The photoluminescences (PL) and the melting temperatures ($T_m$) of the luminescent spiro-dimers obtained from Examples 1-7 were measured, and the results are shown in Table 1. The photoluminescences (PL) shown in table 1 was measured in dichloromethane solvent.

TABLE 1

|  | PL (nm) | Tm (° C.) |
|---|---|---|
| Compound of Example 1 | 390 | 340 |
| Compound of Example 2 | 430 | 310 |
| Compound of Example 3 | 450 | 320 |
| Compound of Example 4 | 480 | 300 |
| Compound of Example 5 | 440 | 350 |
| Compound of Example 6 | 470 | 300 |
| Compound of Example 7 | 425 | 415 |

As shown in Table 1, the luminescent spiro-dimer of the present invention emits high quality blue light, and the melting temperature thereof is more than 300° C. Therefore, the spiro-dimer of the present invention has a superior heat-resistance and stability, and particularly useful for forming an organic layer by a vacuum deposition process. In addition, the luminescent spiro-dimer of the present invention has a superior light-emitting efficiency, and is capable of emitting blue lights of various wavelengths according to the substituent thereof. The luminescent spiro-dimer of the present invention can be applied for various devices, such as a field effect transistor, a photodiode, a photovoltaic cell, a solar cell, an organic laser, a laser diode, and so on.

The invention claimed is:

1. A luminescent spiro-dimer of the following chemical formula, wherein, the linking group K is in which n can be the same or different, and is an integer of 0 to 6, and the linking group K includes at least one group, or
the linking group K is in which n can be the same or different, and is an integer of 0 to 4; R can be the same or different, and is H, halogen, CN, CO$_2$R*, OR*, NR*$_2$, SR*, substituted or non-substituted alkyl group containing from 1 to 4 carbon atoms, substituted or non-substituted aryl or heteroaryl group containing from 4 to 24 carbon atoms, substituted or non-substituted heterocyclic group containing from 4 to 24 carbon atoms, or substituted or non-substituted fused ring group containing from 4 to 24 carbon atoms; and R* can be the same or different, and is H, halogen, substituted or non-substituted alkyl or alkenyl containing from 1 to 6 carbon atoms, substituted or non-substituted aryl or heteroaryl group containing from 4 to 24 carbon atoms, or substituted or non-substituted heterocyclic group containing from 4 to 24 carbon atoms.

2. The luminescent spiro-dimer according to claim 1, wherein the linking group K is and R$_1$ and R$_2$ can be the same or different, and are H, halogen, CN, or alkyl, aryl, alkoxy or heteroaryl group containing from 1 to 10 carbon atoms.

3. An organic light-emitting device comprising:
a first electrode having a high work function;
a second electrode having a low work function; and
at least one organic layer formed between the first electrode and the second electrode, which includes the luminescent spiro-dimer of claim 1.

4. The organic light-emitting device according to claim 3, wherein the luminescent spiro-dimer is used as a host material or a dopant of an organic light-emitting layer.

5. The organic light-emitting device according to claim 3, wherein the luminescent spiro-dimer is used as a host material or a dopant of an organic light-emitting layer and wherein the linking group K is with R$_1$ and R$_2$ can be the same or different, and are H, halogen, CN, alkyl, aryl, alkoxy or heteroaryl group containing from 1 to 10 carbon atoms.

6. The organic light-emitting device according to claim 3, wherein the luminescent spiro-dimer is used to form a hole injecting layer.

7. The organic light-emitting device according to claim 3, wherein the luminescent spiro-dimer is used to form a hole injecting layer and wherein the linking group K is with R$_1$ and R$_2$ can be the same or different, and are H, halogen, CN, alkyl, aryl, alkoxy or heteroaryl group containing from 1 to 10 carbon atoms.

8. The organic light-emitting device according to claim 3, wherein the luminescent spiro-dimer is used to form a hole transporting layer.

9. The organic light-emitting device according to claim 3, wherein the luminescent spiro-dimer is used to form a hole transporting layer and wherein the linking group K is with $R_1$ and $R_2$ can be the same or different, and are H, halogen, CN, alkyl, aryl, alkoxy or heteroaryl group containing from 1 to 10 carbon atoms.

10. The organic light-emitting device according to claim 3, wherein the luminescent spiro-dimer is used to form an electron injecting layer.

11. The organic light-emitting device according to claim 3, wherein the luminescent spiro-dimer is used to form an electron injecting layer and wherein the linking group K is with $R_1$ and $R_2$ can be the same or different, and are H, halogen, CN, alkyl, aryl, alkoxy or heteroaryl group containing from 1 to 10 carbon atoms.

12. The organic light-emitting device according to claim 3, wherein the luminescent spiro-dimer is used to form an electron transporting layer.

13. The organic light-emitting device according to claim 3, wherein the luminescent spiro-dimer is used to form an electron transporting layer and wherein the linking group K is with $R_1$ and $R_2$ can be the same or different, and are H, halogen, CN, alkyl, aryl, alkoxy or heteroaryl group containing from 1 to 10 carbon atoms.

14. The luminescent spiro-dimer of claim 1, wherein the linking group K is in which n and R are as defined above.

15. The luminescent spiro-dimer of claim 2, wherein the linking group K is in which $R_1$ and $R_2$ are as defined above.

16. The luminescent spiro-dimer of claim 2, wherein the linking group K is in which $R_1$ and $R_2$ are as defined above.

* * * * *